United States Patent [19]

Whitcomb et al.

[11] 4,434,647

[45] Mar. 6, 1984

[54] DYNAMIC SPOT CALIBRATION FOR AUTOMATIC PARTICLE COUNTERS

[75] Inventors: William T. Whitcomb, Glendale; John V. Butler, Newhall, both of Calif.

[73] Assignee: Lockheed Corporation, Burbank, Calif.

[21] Appl. No.: 287,238

[22] Filed: Jul. 27, 1981

[51] Int. Cl.³ .......................................... G01N 15/02
[52] U.S. Cl. ..................................... 73/1 R; 356/243
[58] Field of Search ...................... 73/1 R; 356/243; 250/252.1

[56] References Cited

U.S. PATENT DOCUMENTS

| | | | |
|---|---|---|---|
| 2,791,696 | 5/1957 | Schell | 73/1 R X |
| 3,127,464 | 3/1964 | Gustavson | 83/14 |
| 3,412,037 | 11/1968 | Gochman | 252/408 |
| 3,867,835 | 2/1975 | Button | 356/243 X |
| 3,885,415 | 5/1975 | Burns et al. | 73/1 D |
| 4,135,821 | 1/1979 | Pechin et al. | 356/243 X |
| 4,232,967 | 11/1980 | Grachev et al. | 356/243 X |

*Primary Examiner*—E. R. Kazenske
*Assistant Examiner*—Joseph W. Roskos
*Attorney, Agent, or Firm*—Louis L. Dachs

[57] ABSTRACT

The invention is a dynamic spot calibration system (60) and process for calibrating, both for sizing and counting, an automatic particle counter (APC) (42). The APC includes a sensor (38) which uses a light source that focuses through a sensing window (48) onto a sensor element. The system (60) includes a probe (62) which carries a spot (64) of known size. A receiver (66) grips one end of the probe (62) and is attached to an electromagnetic driver (70) which, when activated and driven by an oscillator (72)-amplifier (74) arrangement, interposes the spot (64) into, and out of, the fluid passage defined by the sensing window (48). The probe is precisely positioned in relation to the window (48) by an adjustable mounting system including a pedestal (76), a vertically adjustable arm (78), and a graduated helical rack (84).

28 Claims, 4 Drawing Figures

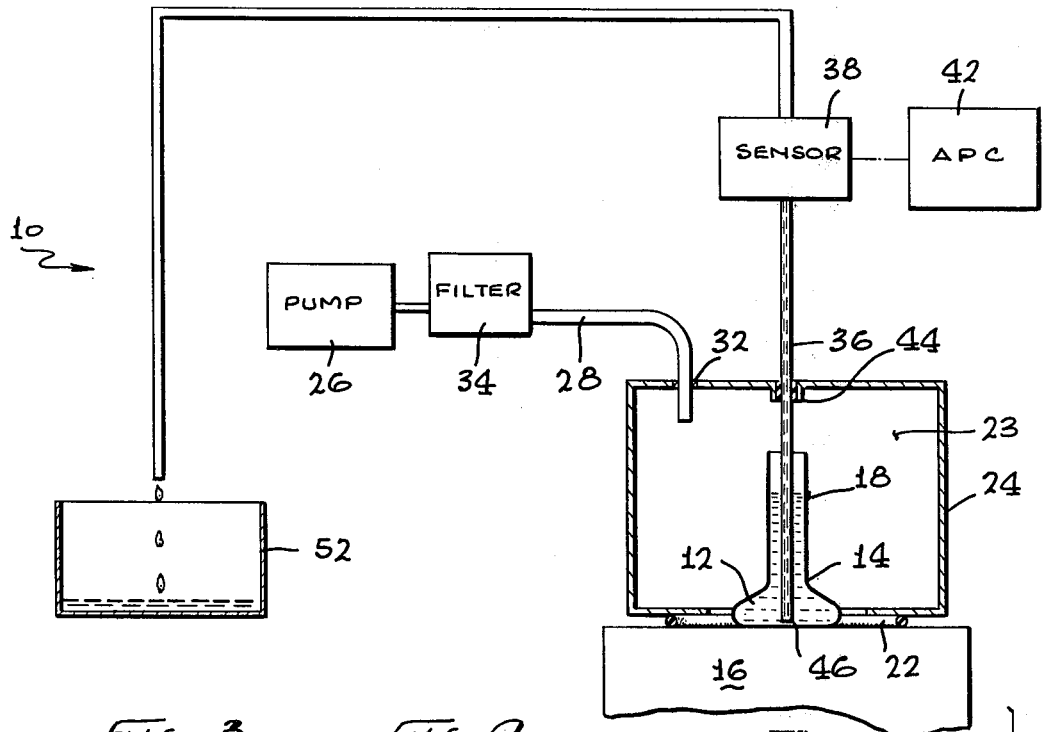
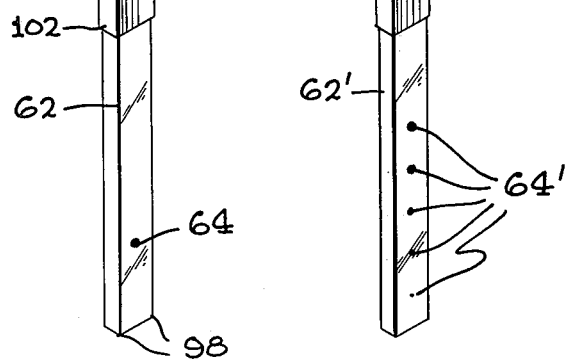
FIG. 3  FIG. 4
FIG. 1
PRIOR ART

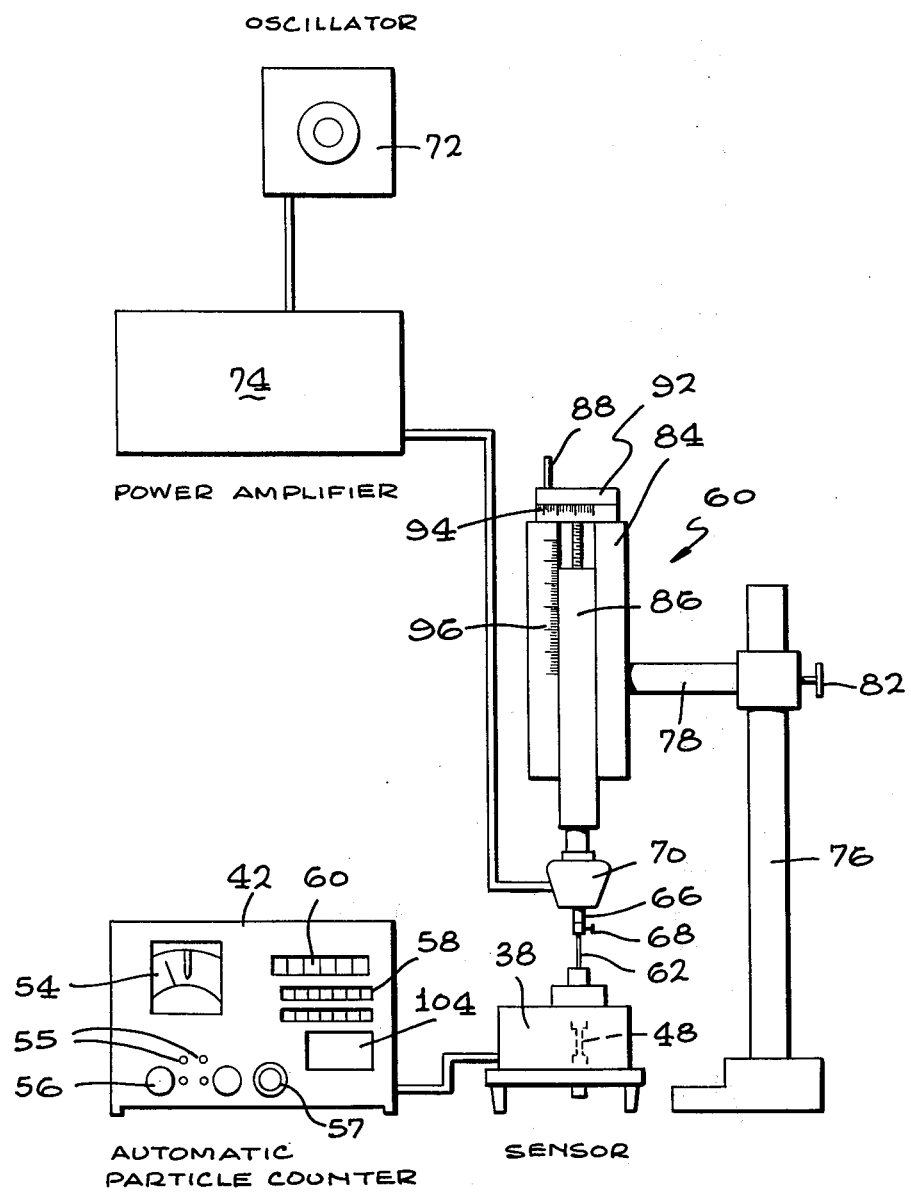

DYNAMIC SPOT CALIBRATION FOR AUTOMATIC PARTICLE COUNTERS

TECHNICAL FIELD

The invention relates generally to a process and apparatus for calibrating automatic particle counters (APCs), and in particular to a process and apparatus for calibrating automatic particle counters which include sensor units containing generally small cross-section sensing window passages for the passing of fluids to be tested.

BACKGROUND ART

In many systems which utilize fluids, such as hydraulic fluids and the like, it is frequently desirable or necessary to monitor and control fluid contamination. This is typically carried out by the controlled passing of a sample of the fluid through a sensor unit which is a part of an automatic particle counter (APC) system. Many of these sensor units, as for example the Royco Model 325 APC sensor unit, are constructed so that the test fluid is passed through a restricted or narrow passage, frequently referred to as a sensing slot or sensing window. The sensor unit operates by sensing the amount of light that is blocked when a particle enters the sensing window fluid passage, where a light source on one side of the window is axially aligned with a light sensor element on the opposite side of the window.

In testing or calibrating the above type of APC, it would of course be highly desirable to use a calibration process and apparatus which is of maximum efficiency and accuracy while at the same time being as simple and economic as possible to provide several prior art processes for calibrating APCs depended on the use of a sample test fluid containing a known quantity of particles of predetermined size. Such calibration and testing systems and procedures typically depended on the use of precision-sized microspheres, which can be quite expensive. Such testing procedures are also typically disadvantaged because of other considerations such as test sphere availability and handling problems, long calibration times, accuracy problems, and problems relating to maintaining suitable cleanliness of the test area and preventing extraneous contamination.

One prior art approach to calibrating a particle counting apparatus using a sample test fluid approach similar to the aforementioned testing procedures is disclosed in U.S. Pat. No. 3,412,037 to Gochman et al. The APC unit that is to be calibrated operates on a flow of diluted blood that is passed through a flow cell of small cross-section. Illuminated optical means are coupled to the flow-cell and detect the passage of individual blood cells therethrough, providing an output pulse signal in response to the passage of the blood cells. U.S. Pat. No. 3,412,037 is primarily directed to the provision of a standard fluid which approximates blood cells in blood, and which can then be used to calibrate the APC. The standard comprises a suspension of minute unicellular fungi in a solution of sodium chloride in a concentration of 5 to 15%, and sodium flouride in a concentration of one half of 1% or greater.

A somewhat different approach to calibration, which is utilized to calibrate a particle velocity measuring instrument rather than an APC, is disclosed in U.S. Pat. No. 3,885,415 to Burns et al. In the U.S. Pat. No. 3,885,415 calibrating system, a movable rotatable calibration disc is generally disposed and moved within and through the optical viewing path of an analytical system devoted to calculating particle related information. A predetermined number of contrast regions representing particles are located upon the surface of the disc, and when the disc is rotated at a given rate within the optical viewing path it simulates predetermined particle movement enabling calibration of the analytical devices. The U.S. Pat. No. 3,885,415 calibrating system calibrates fluid borne colloidal suspension velocities, and is not concerned with the size measurement or quantity of particulate matter in a fluid.

Another calibration system which utilizes a rotating disc is disclosed in U.S. Pat. No. 3,127,464 to Gustavson. In this patent, the aerosol particle counter that is being calibrated is designed to sense light reflected from particles in a target area. The device attempts to simulate the reflections by transmitting portions of the light beam through apertures of known sizes, then redirecting them to a sensor. The system only simulates a calibration, and assumes that all particles of equal size will have equal reflective characteristics regardless of the shape, texture, or color. It is intended that any device using the method of U.S. Pat. No. 3,127,464 be configured so the path of the reflected light is at an angle to the path of light from the light source, so that the paths are not in axial alignment.

The APC device to be calibrated by the calibration system and device of the present invention is not a particle velocity measuring instrument as in U.S. Pat. No. 3,885,415, and is not a simulation system as in U.S. Pat. No. 3,127,464. The APC systems which are to be calibrated in accordance with the present invention sense the amount of light that is blocked when a particle enters an optically monitored reduced cross-section sensing slot or window, where the light source and sensor are in axial alignment. Rather than simulating reflections as in U.S. Pat. No. 3,127,464 or simulating contrast areas moving with known velocity as in U.S. Pat. No. 3,885,415, the APC of the present invention is calibrated by the placing of a single opaque spot in the path of a light beam whose optical system is in axial alignment, blocking the exact amount of the light as a particle with the same cross-sectional area. This enables an absolute and true sizing calibration of the APC. In addition, neither of the discs in U.S. Pat. Nos. 3,885,415 and 3,127,464 is adaptable for use in the sensing slots or windows of the sensor units of the APCs being calibrated in accordance with the present invention.

In view of the problems and requirements to be met in calibrating APC devices having optical type sensors which operate with reduced cross-section sensing windows, and the desire for less costly, time consuming and complex calibrations systems, there is a need for a simplified, economical, fast and efficient (accurate) sizing and calibration apparatus and process for calibration of automatic particle counters. Ideally, the calibration system and process should be readily adaptable to a relatively non-complex testing environment and to a variety of different models of Automatic Particle Counters available on the market today.

From the foregoing, it can be seen that it is a primary object of the present invention to provide a calibration system and process for one in calibrating APCs of the type having sensor units which utilize reduced cross-section sensing windows for the passage of test fluids.

It is also an object of this invention to provide a calibration system which is economic to provide and operate, and which is efficient and precise in calibrating various APC models.

It is another object of the present invention to provide calibration system and process for calibration of APCs, which can be utilized in a conveniently operated manner without time consuming, costly, and complex operations directed at maintaining the cleanliness of the testing area, and which minimizes cleanliness and contamination problems normally associated with APC calibration operations.

It is yet another object of the present invention to provide a system and process for calibration of APCs which eliminates the need for precision-sized and shaped spheres and particles.

It is another object of this invention to provide an apparatus that enables fast and precise calibration of the electronic and optical components of standard APC units.

DISCLOSURE OF INVENTION

The invention is directed to an apparatus and process for calibrating an Automatic Particle Counter system which includes a sensor unit having a generally small cross-section sensing window. The apparatus includes a probe of a cross-section smaller than but approximating the cross-section of the sensing window, and an oscillator - driver mechanism for interposing a portion of the probe into and out of the sensing window area of the APC. The probe portion which is to be interposed into the sensing window is provided on one surface with a single, opaque, precisely sized circular spot. By moving the probe upwards and downwards in the sensing window of the APC, the spot can be made to pass through the light beam of the sensor device and produce an electrical pulse. The magnitude of the pulse can then be accurately determined, or re-set, for the diameter of the spot being used.

The driver comprises a permanent magnet type shaker and is positioned between the end of a precision position set device and an end of the probe. The oscillator is a low-frequency oscillator and is provided to drive the shaker and pass the spot on the probe through the sensing window. The probe itself is clear and may be constructed of plastic or glass.

The novel features which are believed to be characteristic of the invention, both as to its organization and its method of operation, together with further objects and advantages thereof, will be better understood from the following description, taken in connection with the accompanying drawings in which a presently preferred embodiment of the invention is illustrated by way of example. It is to be expressly understood, however, that the drawings are for purposes of illustration and description only, and are not intended as a definition of the limits of the invention.

BRIEF DESCRIPTION OF DRAWINGS

FIG. 1 is a schematic representation generally showing a prior art system for particle contamination testing of a fluid specimen;

FIG. 2 is a schematic representation of the calibration system of the present invention being arranged to calibrate the Automatic Particle Counter shown in FIG. 1;

FIG. 3 is a perspective view of a calibration probe in accordance with a first embodiment of the present invention; and FIG. 4 is a perspective view of a calibration probe in accordance with a second embodiment of the present invention.

BEST MODE OF CARRYING OUT THE INVENTION

Referring now to the drawings, wherein like numerals denote like parts, FIG. 1 depicts a prior art contamination testing system (10) for particle contamination testing of a fluid specimen (12). In testing for contamination, the specimen (12) is placed in a sample bottle (14) which is placed upon a movable platform (16) when it is in the down position (shown in phantom). After the bottle (14) is filled, typically to a fluid level of 100 ml, marked at (18) on the bottle (14), the platform (16) is raised to its upper position. In its raised position, the platform (16) forms a seal, via an O-ring seal (22), with a clear plastic or glass container (24).

A pump (26) is provided for alternatively pulling a vacuum in and pressurizing the container (24) via the line or tube (28), which is sealed within an opening in the container (24) via a seal (32). In order to avoid contamination of the chamber (23) within the container (24), a filter unit (34) is provided. When the pump (26) pulls a vacuum, the fluid specimen is degassed and any bubbles within the fluid are removed. Such bubbles can give a false reading in that they can appear to be contamination particles to the particle counting test equipment.

When the pump (26) pressurizes the chamber (23), the fluid specimen (12) is driven up through a tube (36) connected to a sensor unit (38) which provides electronic signals to an automatic particle counter (42). The tube (36) is also sealed within an opening in the container (24) via a sealing member (44), and the bottom of the tube (46) is maintained as close to the bottom of the sample bottle (14) as is practically possible. The fluid specimen (12) flows through a sensing window (48) within the sensor unit (38), (shown in phantom in FIG. 2), and then into a catch container (52). Test system (10) typically contains other elements, such as photocell units to monitor the amount of fluid and to turn the APC (42) on and off after the desired amount of fluid is tested, but description of such elements is not necessary for a full and complete understanding of the present invention, and are not shown therefore in FIG. 1.

During operation the APC (42) and sensor unit (38) utilize an optical system (not shown) which shines light through the sensing window (48) and therefore through the fluid passageway formed by the window. Any particles or other elements which block off a percentage of the light causes the sensor unit (38) to put out a pulse signal whose amplitude is proportional to the particle size. This signal is delivered to the APC (42) which records how many particles in certain desired size ranges there are in 100 ml of fluid specimen tested. For example, it might typically be desired to test for how many particles there are in the ranges of 5-15 microns, 15-25 microns, 25-50 microns, 50-100 microns, and greater than 100 microns, in 100 ml of fluid specimen. Thus the present invention will be described hereinafter in conjunction with calibrating the APC (42) to test for particles in these size ranges.

The dynamic spot calibration system (60) of the present invention, shown in FIG. 2, consists of an accurately sized glass (or plastic) probe (62) of a cross-section approximately the same as, but somewhat smaller than, the cross-section of the sensing window (48), and further includes a device for introducing the probe into the sensing window (48). The probe (62) is shown optically flat on all faces and free from surface imperfections, and includes a single, opaque, precisely sized circular spot (64), which has been placed or formed on one surface thereof (FIG. 3). When the spot (64) is moved upwards and downwards in the sensing window (48) of the sensor unit (38), it passes through the optic system light beam and produces an electrical pulse. The magnitude of the pulse can then be accurately determined, or re-set, for the diameter of the spot being used for calibration.

In the embodiment shown in FIG. 2, the probe (62) is held within a receiver (66) by a set screw (68). The receiver (66) is part of a permanent magnet shaker or electromagnetic driver unit (70) which is arranged to introduce the probe into the sensing window (48), and to reciprocate the spot (64) through the sensor light beam. The electromagnetic driver (70) is driven by means of a low-frequency oscillator (72) via a power amplifier (74) producing the required sine wave power output to drive the electromagnetic driver (70).

While the APC (42) may be any type of particle counter which utilizes an optical or similar sensor arrangement, the general face layout of a Royco Model 325 is shown in FIG. 2. The sensing window in a Royco Model 325 APC sensor (38) is approximately 0.5 mm × 1.0 mm in size, so the passing of the probe (62) through the window has to be conducted with extreme delicacy to avoid fracture of the glass probe. (This problem is somewhat reduced by utilization of a plastic probe.) In any event, use of a sensitive mechanical positioning device, similar to the focusing mechanism of a microscope (FIG. 2), can be utilized to alleviate this problem. Details of the location and operation of such elements of the APC (42) as the calibration meter, several switches, fluid calibration adjustment knob, amplitude adjustment knob, channel selector buttons, and digital count display, (54)–(59) schematically shown, are not necessary for a clear understanding of the operation of the present invention.

The positioning device of the instant invention is shown to include (FIG. 2) a pedestal base (76), having an arm (78) extending therefrom. The arm (76) is adjustable upward or downward via a set screw (82). Secured to the arm (76) is a graduated helical rack (84), the central element (86) of which is secured to and supports the electromagnetic driver (70). The central element (86) is vertically movable via a turn handle (88) secured to a turn member (92). The graduated helical rack includes two scales (94), (96) which provide a precise registration and adjustment means, the use of which will be described hereinafter.

As stated hereinabove the dimensions and cross-section of the probe (62) should ideally approximate the fluid passageway in the sensing window (48). In any case, it has been found that at the time the glass or plastic probe (62) is highly polished, care should be taken to make sure that the edges (98) (FIG. 3) of the probe are even, smooth and precise. This is particularly important when the probe (62) is used to calibrate for particularly small particle ranges, for example the 5–15 micron range. When working with a 5 micron spot, variations in the edges (98) of the probe (62) can and do adversely affect the count, that is, thinning or thickening on both edges of the probe (62) may alter the count obtained during calibration.

While the probe (62) could be made up as an integral unit, it has been found desirable to utilize a sleeve (102) over one end of the probe (FIG. 3). The sleeve serves several purposes among which is included the use of the sleeve to handle the probe (cleanliness), and protection of the probe when the thumb screw (68) is tightened down to hold the probe in the receiver (66).

When a standard set of probes (62) is produced to calibrate for the 5 example ranges specified hereinabove, that is, five probes having one spot each of 5, 15, 25, 50 and 100 micron size, respectively, they can be made to uniformly abut against a stop within the receiver (66), or with a scribe line (for easy position reference). In either case, the location of the spot (64) from some reference point of the receiver (66) is known. In addition, the frequency and amplitude of the vertical excursions of the receiver (66) and probe (62) can be set and controlled at the oscillator (72) and amplifier (74). The dynamic spot calibration system (60) is thus readily adaptable to repeat calibration operations.

The various APCs on the market today do not have standard shape and dimension sensing windows. However, for each APC model and therefore each set of sensing window parameters, a different set of probes (62) can be provided and utilized. Once the system has been set up and run, a record can be kept of what settings on the scales (94) and (96) should be utilized for a specific probe set, APC unit, at specified oscillator and amplifier settings. Repetition via future calibrations is then simplified, and minor adjustments can readily be made by operation of the turn member (92), which can be moderately adjusted when the oscillator (72) is on.

FIG. 4 depicts an alternative to using a specific set of probes for each model APC being calibrated. In accordance with this embodiment, a single probe (62') is provided with five distinct spots 64'. These spots can be, for example of five sizes, 5, 15, 25, 50 and 100 microns, and can be utilized to calibrate the APC (42) to the five particle ranges discussed hereinabove. In this case, scale (94), (96) settings would have to be established for each spot (64'). However, the need to keep a set of probes for each APC unit is eliminated, and removal and insertion of a new probe for each particle range calibration is eliminated. It should of course be readily apparent that the size and number of spots utilized on either the probe (62) or the probe (62') is entirely up to the calibrator and tester, and can be altered as desired for different APC units and calibration ranges.

The spots 64 and 64' can be produced on any suitable manner, and in the case of plastic and glass probes, etching the spots in the surface of the probe has been found to be quite effective. When etching is used, the likelihood of removal or wearing and therefore altering of the spot(s) is lessened a great deal.

The process, in accordance with the present invention, of calibrating the APC (42) for the above five particle ranges would be carried out as follows:

(1) A set of five probes (62), each having spots of 5, 15, 25, 50 and 100 microns respectively, is provided.

(2) For calibrating the APC (42) to the 5–15 micron particle range, a probe having a 5 micron spot is inserted in the receiver (66) and secured therein by the thumb screw (68). (The probe can be inserted using a stop or scribe line as discussed hereinabove to provide a standard for future calibration of the APC at the selected particle size range.)

(3) An initial approximation or setting of the probe spot relative to the sensing window (48) can be carried out by adjusting the arm (78) on the pedestal base (76) and/or by rotating turn number (92). (For standard settings, a reading of scale (96) may now be taken and recorded.)

(4) The oscillator (72) and amplifier (74) are set to provide the desired frequency and amplitude of the vertical excursions of the probe (62). Frequencies of from about 5 to 30 CPS have been found to be quite satisfactory, and the vertical distance the spot is moved should be adjusted so that it enters and clears the optical sensor element (aperture) of the sensing window (48). (Again, for standard settings, the settings can be recorded.)

(5) Knowing the size of the spot (64), the APC (42) is set to the channel that is being counted in.

(6) The system is turned on, and the vertical positioning of the spot (64) is finally and precisely adjusted by adjusting turn member (92) till the APC (42) starts counting. (For standardizing positioning of the spot (64) relative to the sensing window (48) the reading of scale (94) is recorded.)

(7) The adjustment control that changes the amplitude of pulses generated by the APC (42) is now adjusted to set up the threshold level for the range being counted in. This is done by backing off on the threshold setting till the signal (count) disappears for the 5 micron spot and then going forward till the count first resumes. The APC (42) is now calibrated for the 5–15 micron range.

Various APC models have different threshold adjustment means. For purposes of the present description, the APC (42) is assumed to be provided with threshold adjustment screws (not shown) located behind the window (104). Note, this adjustment might have to be used in step (6) to get the APC (42) to start counting for a selected spot size.

(8) When the final settings are made to the travel of the spot (64) and the threshold setting of the APC (42), the timer of the APC (42) can be run for a set time, for example one minute. Knowing the frequency of the oscillator, and the time the spot is run through the sensing window, the exact count the machine should read is known (the count in the selected channel is equal to two times the frequency). The APC (42) is thus not only calibrated, but tested for count accuracy.

(9) The first eight steps can be repeated for each probe (62) having a different size spot (64), thereby calibrating and checking the APC count for as many ranges as there are probes or spots (64).

Once all the threshold levels of the APC (42) have been calibrated, and the various arm (78) and scale (94), (96) settings have been established, the APC (42) can be re-calibrated without the major probe adjustment steps above, other than perhaps minor adjustments via the turn member (92).

Under the present calibration system and process, the APC (42) receives pulses from the sensor (38) having an amplitude proportional to the diameter of the spot (64), and the number of pulses will be equal to double the input frequency. The sizing threshold level can be adjusted to the pulse amplitude, and the count verified using the APC built-in timer (generally standard). A calibrator having a spot diameter of appropriate size must be used to calibrate each size range, or channel of the APC. The APC internal calibrator can then be used to determine the exact trigger levels for each channel expressed in millivolts, or calibration number. A calibration curve can then be plotted using the above calibration numbers vs. calibrator spot sizes. From this curve it is possible to obtain the values to set the channels of the APC to conform to standard particle counting ranges.

The dynamic spot calibration system and process of the present invention provides several benefits over known calibration systems. The calibration system affects only the optics and electronic sections of the APC system, and provides a very fast and precise calibration of the sizing or trigger level amplitude settings of the APC. The need for precision-sized spheres, and their attendant cost and handling problems, is eliminated. In addition, the need for operating in a clean room is eliminated by utilization of a laminar flow bench for provision of a suitably clean environment, which is sufficient in most instances. Finally, the APC is quickly and efficiently calibrated both for sizing and counting.

It is apparent that there has been provided with this invention a novel dynamic spot calibration system and process for APCs which fully satisfies the objects, means and advantages set forth hereinbefore. While the invention has been described in combination with specific embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims.

INDUSTRIAL APPLICATION

The dynamic spot calibration system and process of the present invention is useful in calibrating, both for sizing and counting, automatic particle counters used to test fluid samples for various types of particle content.

We claim:

1. A dynamic calibration system for calibrating an automatic particle counter having a sensor unit including a sensor window defining a fluid passage, said sensor unit including means to sense the size of particles contained in a fluid passing through said window and being adapted to generate signals representative thereof, comprising:
   at least one probe having a portion adapted to be inserted into and out of said sensor window fluid passage, said at least one probe constructed of transparent material;
   means associated with said probe portion for simulating particles of a preselected size, said simulating means comprising an opaque spot located along said probe portion;
   means for gripping said probe;
   means connected to said gripping means for reciprocally driving said probe portion within said sensor fluid passage;
   means associated with said driving means for providing power to said driving means; and
   means connected to said driving means for precisely positioning said at least one probe portion relative to said sensor window fluid passage.

2. A dynamic calibration system as in claim 1 wherein said at least one probe comprises an elongated member comprising said portion and an end portion adapted to be gripped by said gripping means.

3. A dynamic calibration system as in claim 2 wherein said at least one probe includes a protective element remote from said probe portion to prevent damage by said gripping means.

4. A dynamic calibration system as in claim 3 wherein said protective element comprises a protective sleeve element positioned around said probe end portion.

5. A dynamic calibration system as in any one of claims 2 or 3 wherein said at least one probe comprises one probe having a plurality of predetermined different size spots, each of said plurality of spots being of a size to simulate particles of different preselected sizes.

6. A dynamic calibration system as in any one of claims 1, or 2 wherein said at least one probe is constructed of glass.

7. A dynamic calibration system as in any one of claims 1, or 2 wherein said at least one probe is constructed of plastic.

8. A dynamic calibration system as in claim 1 wherein said driving means comprises an electromagnetic driver.

9. A dynamic calibration system as in claim 8 wherein said gripping means comprises a receiver element connected to said electromagnetic driver.

10. A dynamic calibration system as in claim 9 wherein said calibration system includes means for providing for uniform insertion of different probes into said receiver.

11. A dynamic calibration system as in claim 10 wherein said means for providing uniform insertion comprises a stop element associated with said receiver.

12. A dynamic calibration system as in claim 10 wherein said means for providing uniform insertion comprises at least one mark on each of said probes.

13. A dynamic calibration system as in claim 8 wherein said power supplying means includes control means for controlling said electromagnetic driver, whereby the frequency and amplitude of the excursion of said particle simulating means are maintained at a predetermined value.

14. A dynamic calibration system as in claim 13 wherein said control means comprises an oscillator/amplifier system.

15. A dynamic calibration system as in claim 1 wherein said sensing means includes an optical system having a light beam-generating light source and a sensor element in axial alignment, said driving means, power supplying means, and positioning means being adapted and adjustable to cause said particle simulating means to intercept the path of said light beam when said power supplying means is turned on.

16. A dynamic calibration system as in claim 15 wherein said positioning means comprises a graduated helical rack.

17. A dynamic calibration system as in claim 16 wherein said graduated helical rack includes at least one scale for providing precise positioning of said particle simulating means relative to said light beam axis.

18. A dynamic calibration system as in claim 1 wherein said power means comprises an oscillator.

19. A calibration kit for dynamic calibration of automatic particle counters having a sensor window of reduced cross-section comprising:
at least one elongated probe element of a size and cross-section smaller than, but approximating the size and cross-section of, said sensor window, said probe element including at least one opaque spot on a portion thereof for simulating particles of a preselected size;
a receiver mechanism adapted to receive and grip one end of said at least one elongated probe element;
a driver mechanism actively attached to said receiver;
a power source for activating said driver mechanism whereby said driver mechanism moves said receiver reciprocally at a desired frequency and amplitude; and
a positioning device secured to said driver/receiver mechanisms for establishing the exact position and path of travel of said probe element within said reduced cross-section.

20. A calibration kit as in claim 19 wherein said at least one elongated probe element comprises a single transparent probe having a plurality of spots each of different preselected sizes than the remaining spots whereby a single probe element can be utilized to calibrate said automatic particle counter for different particle sizes.

21. A calibration kit as in claim 19 wherein said at least one elongated probe element comprises a plurality of transparent probe elements, each having a single spot of a different preselected size than the spots on the remaining probes, whereby by interchanging said plurality of probe elements, said kit can be utilized to calibrate said automatic particle counter for different particle sizes.

22. A calibration kit as in any one of the claims 19, 20, or 21 wherein said probe elements are glass and said spots are opaque circular spots.

23. A calibration kit as in any one of claims 19, 20, or 21 wherein said probe elements are plastic and said spots are opaque circular spots.

24. A calibration kit as in claim 19 wherein said driver mechanism comprises an electromagnetic driver and said power source comprises an oscillator/amplifier system.

25. A calibration kit as in claim 19 including a sleeve element adapted to fit over said one end of said at least one elongated probe element.

26. A calibration kit as in claim 19 wherein said positioning device comprises a graduated helical rack.

27. A process for calibrating an automatic particle counter having a sensor unit including a sensor window defining a fluid passage, said sensor unit including sensing means to sense the size of particles contained in fluid passing through said window and being adapted to generate pulse-signals representative thereof, said particle counter further including pulse-signal amplitude adjustment means and particle count read-out means, comprising the steps of:
providing an elongated probe element having at least one spot on a portion thereof, said spot being of a size to simulate a preselected particle size for which said automatic particle counter is to be calibrated, said probe element portion being of a size and cross-section smaller than, but approximately the size and cross-section of, said sensor window fluid passage;
reciprocally moving said probe portion within said sensor window fluid passage such that said at least one spot is moved into and out of said passage and said sensing means begins to intermittently generate said signals;
backing off on said pulse-signal amplitude adjustment means until the generation of said signals stop and said automatic particle counter stops counting; and
slowly advancing the setting of said pulse-signal amplitude adjustment means until said automatic particle counter just resumes counting, whereby a threshold level is established and said automatic particle counter is calibrated for the preselected particle range established by said at least one spot size.

28. A process for calibrating as in claim 27 wherein after said automatic particle counter is calibrated for said preselected range, the following steps are carried out:

reciprocally moving said probe portion within said sensor window fluid passage at a preselected frequency such that said at least one spot is moved into and out of said passage at a known number of times per unit of time; and operating said particle count read-out means to count the number of times said at least one spot is sensed over a preselected period of time, whereby said automatic particle counter is tested for count accuracy.

* * * * *